(12) United States Patent
Javey et al.

(10) Patent No.: US 11,774,399 B2
(45) Date of Patent: Oct. 3, 2023

(54) INVERSION LAYER GAS SENSORS USING BULK SILICON CHEMICAL SENSITIVE TRANSISTORS

(71) Applicant: The Regents of the University of California, Oakland, CA (US)

(72) Inventors: Ali Javey, Lafayette, CA (US); Hossain Mohammad Fahad, Berkeley, CA (US); Niharika Gupta, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 262 days.

(21) Appl. No.: 16/958,676

(22) PCT Filed: Dec. 27, 2018

(86) PCT No.: PCT/US2018/067741
§ 371 (c)(1),
(2) Date: Jun. 27, 2020

(87) PCT Pub. No.: WO2019/133748
PCT Pub. Date: Jul. 4, 2019

(65) Prior Publication Data
US 2021/0063345 A1   Mar. 4, 2021

Related U.S. Application Data

(60) Provisional application No. 62/611,008, filed on Dec. 28, 2017.

(51) Int. Cl.
*G01N 27/414*   (2006.01)
*G01N 33/00*    (2006.01)

(52) U.S. Cl.
CPC ..... *G01N 27/4141* (2013.01); *G01N 33/0032* (2013.01)

(58) Field of Classification Search
None
See application file for complete search history.

(56) References Cited

U.S. PATENT DOCUMENTS

2007/0007546 A1* 1/2007 Goto ............... G01N 27/4141
                                                    257/147
2008/0265985 A1* 10/2008 Toumazou ......... G01N 27/4148
                                                    204/417

(Continued)

FOREIGN PATENT DOCUMENTS

JP         4224294 B2      2/2009
WO    WO-2015187878 A1 * 12/2015 ......... G01N 27/4141

OTHER PUBLICATIONS

Fahad et al., Room temperature multiplexed gas sensing using chemical-sensitive 3.5-nm-thin silicon transistors, Applied Sciences and Engineering, Science Advances, Mar. 24, 2017 [retrieved on Feb. 20, 2019]. Retrieved from the internet:<URL:http://advances.sciencemag.org/content/advances/3/3/e1602557.full.pdf>pp. 1-8.

(Continued)

*Primary Examiner* — Erik Kielin

(57) ABSTRACT

A gas sensor and methods for producing the same are disclosed. The gas sensor of the present disclosure includes a bulk silicon layer, comprising a controllable inversion layer, an oxide layer on top of the bulk silicon layer, wherein the controllable inversion layer is located at an interface of the bulk silicon layer and the oxide layer, and a sensing layer on the oxide layer, wherein a sensitivity of the sensing layer is a function the controllable inversion layer.

11 Claims, 7 Drawing Sheets

(56) References Cited

U.S. PATENT DOCUMENTS

| | | |
|---|---|---|
| 2012/0055236 A1 | 3/2012 | Takulapalli |
| 2013/0186178 A1* | 7/2013 | Usagawa ............... G01N 27/06 |
| | | 73/31.06 |
| 2013/0313569 A1* | 11/2013 | Usagawa ............... H01L 29/78 |
| | | 257/253 |
| 2014/0131774 A1 | 5/2014 | Lee et al. |
| 2016/0097731 A1 | 4/2016 | Usagawa |

OTHER PUBLICATIONS

Fahad et al., Highly Sensitive Bulk Silicon Chemical Sensors with Sub-5 nm Thin Charge Inversion Layers, ACS Nano., Feb. 17, 2018 [retrieved on Feb. 20, 2019]. Retrieved from the internet:<URL:http://nano.eecs.berkeley.edu/publications/ACSNano_2018_bulk%20Si%20CSFET.pdf> pp. A-G.

Int'l Search Report and Written Opinion for PCT/US2018/067741 dated Mar. 19, 2019.

* cited by examiner

INVERSION LAYER GAS SENSORS USING BULK SILICON CHEMICAL SENSITIVE TRANSISTORS

CROSS REFERENCE TO RELATED APPLICATIONS

This application claims priority under 35 U.S.C. § 119(e) to U.S. provisional patent application Ser. No. 62/611,008, filed on Dec. 28, 2017, which is hereby incorporated by reference in its entirety.

FIELD OF THE INVENTION

The present disclosure relates generally to transistor gas sensors and methods for producing the same.

BACKGROUND

In recent years, micro-hotplate based resistive ceramic gas sensing has been the dominant commercial technology for miniaturized low power gas sensing applications. These sensors are made of thick (hundreds of nanometers) films of transition metal oxides, for example ZnO, $SnO_x$ and $InO_x$, that get oxidized or reduced by a target gas at high temperatures. Consequently, this technology suffers from high power consumption requirements (>>1 milliwatt (mW)). Furthermore, such ceramic films need to be electrically conductive, thereby limiting the choice of metal oxides which can be used for sensing, as well as leading to poor selectivity against interfering gases. Despite these drawbacks, major manufacturers continue to develop portable gas sensors based on this technology.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
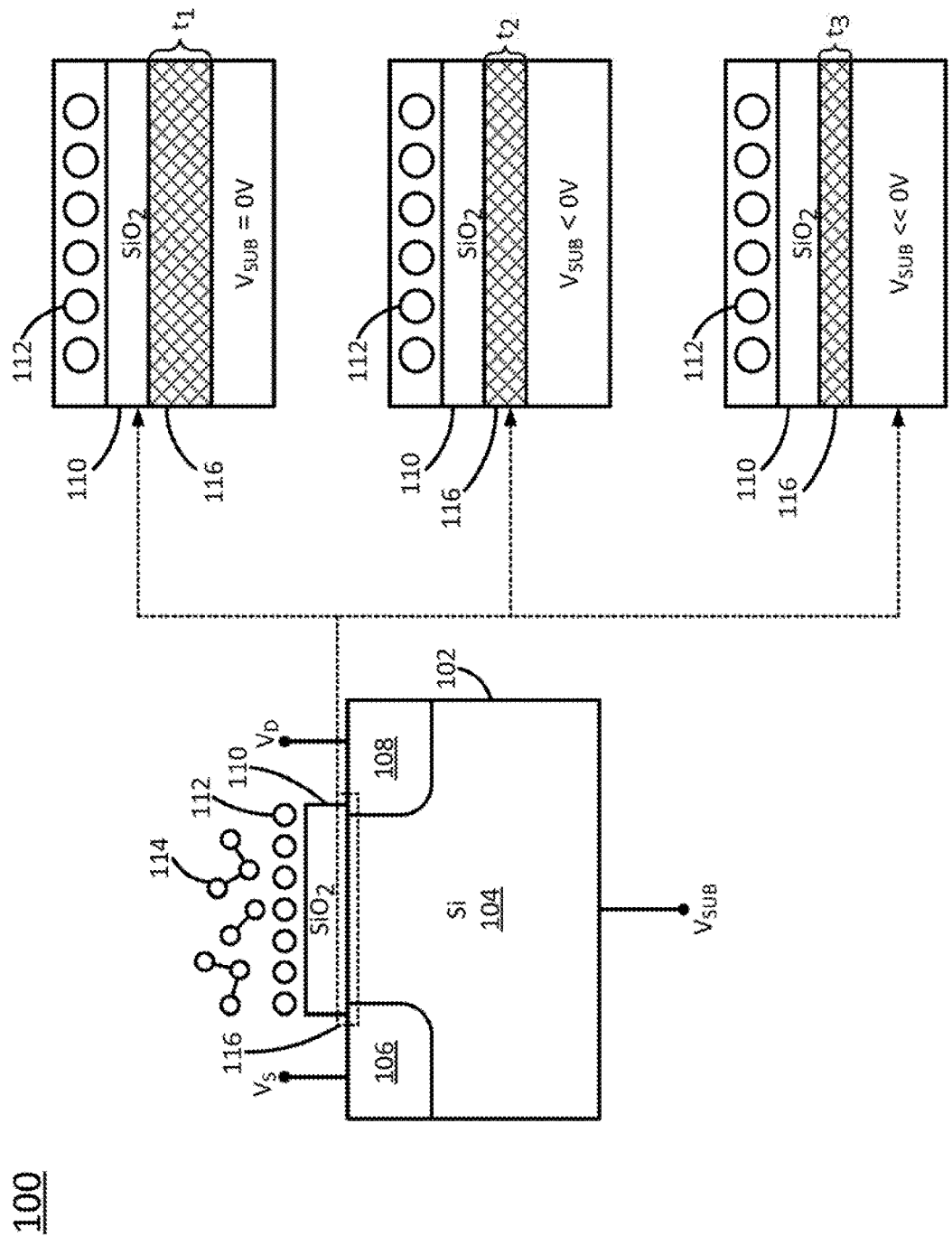
FIG. 1 illustrates a cross-sectional schematic of an example bulk silicon chemical sensitive field effect transistor (CS-FET) with an electrically floating ultra-thin sensing layer of the present disclosure.

The present disclosure provides inversion layer gas sensors using bulk silicon chemical sensitive transistors and methods for producing the same. For example, the present disclosure may leverage the design and fabrication of metal-oxide-semiconductor (MOS) field-effect transistors (FET) to detect gas molecules. The design of the MOSFET can be modified with an additional sensing layer. The sensitivity of the sensing layer can be tuned by controlling a voltage that is applied to an inversion layer in the transistor, as discussed below. Thus, the gas sensors of the present disclosure are cheaper and easier to build than chemical FETs that are used to detect gas molecules.

As discussed above, micro-hotplate based resistive ceramic gas sensing has been the dominant commercial technology for miniaturized low power gas sensing applications. These sensors are made of thick (hundreds of nanometers) films of transition metal oxides, for example ZnO, $SnO_x$ and $InO_x$, that get oxidized or reduced by a target gas at high temperatures. Consequently, this technology suffers from high power consumption requirements (>>1 milliwatt (mW)). Furthermore, such ceramic films need to be electrically conductive, thereby limiting the choice of metal oxides which can be used for sensing, as well as leading to poor selectivity against interfering gases. Despite these drawbacks, major manufacturers continue to develop portable gas sensors based on this technology.

Compared to resistive ceramic gas sensors, FET (field effect transistor) technology has significant technological advantages for low power, miniaturized gas sensing applications. FET gas sensors based on low dimensional nanomaterials such as CNTs, silicon nanowires, graphene, and TMDs have shown significant promise in sensitively detecting a wide variety of gases at room temperature. This is primarily due to: a) large surface-volume ratio and b) confinement of charge transport in one (CNT, silicon nanowire) or two dimensions (graphene, TMDs). Among these materials, pristine silicon (silicon <100>) is comparatively inert and can only respond to specific gases upon functionalization with appropriate chemical sensitive layers. Recently, this this selectivity advantage of silicon with ultra-thin-body (3.5 nm) silicon CS-FETs integrated with different chemical sensing layers (~5 nm thin metal alloys) sensitive to specific gases was demonstrated.

The present disclosure demonstrates bulk silicon CS-FETs as a highly sensitive low power gas sensing platform. Through simulations and experiments, the present disclosure shows that the silicon channel in CS-FETs does not have to be physically thin, and that bulk silicon can provide a similar high sensitivity advantage through the electrostatic control of thin inversion layers. To evaluate this sensor platform, hydrogen gas sensing is used as the test application. This is because monitoring hydrogen leaks is becoming increasingly important in a number of applications, where the current market requires stable sensors that can detect below the lower explosion limit of 4% (v/v in air) at low power, low cost and in a very small form factor.

Conceptually, bulk silicon CS-FETs are similar to conventional enhancement-mode silicon transistors with the exception of the electrically active gate stack that is replaced by a large surface area, ultra-thin chemical sensing layer as depicted in FIG. 1. FIG. 1 illustrates an example of a gas sensor 100 that is fabricated from a bulk silicon CS-FET. In one example, the gas sensor 100 may include a bulk silicon substrate 102, a body portion 104, one or more wells 106 and 108, an oxide layer 110, and a sensing layer 112. The sensing layer 112 may be used to detect gas molecules 114.

In one example, the gas sensor 100 may have a controllable inversion layer 116. A thickness of the controllable inversion layer 116 may be controlled based on an amount of voltage that is applied to vary a level of sensitivity of the sensing layer 112. In one example, a voltage $V_{sub}$ may be applied to the body 104 to control the thickness of the controllable inversion layer 116, and thereby the sensitivity of the sensing layer 112.

In one example, the wells 106 and 108 may be n-doped or p-doped. If the wells 106 and 108 are n-doped, the body 104 may be slightly p-doped. In addition, the controllable inversion layer 116 may be controlled by a negative voltage, $V_{sub}$. If the wells 106 and 108 are p-doped, the body 104 may be slightly n-doped. In addition, the controllable inversion layer 116 may be controlled by a positive voltage, $V_{sub}$. In one example, a voltage $V_D$ may be applied to the well 108 and a voltage $V_S$ may be applied to the well 106.

FIG. 1 illustrates how different amounts of voltages of $V_{sub}$ may affect a thickness "t" of the controllable inversion layer 116. In one example, the wells 106 and 108 may be n-doped and the voltage $V_{sub}$ may be a negative voltage. In one example, when $V_{sub}=0$ the controllable inversion layer 116 may have a thickness $t_1$. The thickness $t_1$ may have a greatest thickness and cause the sensing layer 112 to have a least amount of sensitivity to the gas molecules 114.

When $V_{sub}$ is applied and greater negative voltages that are less than 0 are applied, the controllable inversion layer 116 may shrink to a thickness $t_2$, where $t_2<t_1$. As the thickness of the controllable inversion layer 116 decreases, the sensitivity of the sensing layer 112 may increase.

When large amounts of negative voltage, $V_{sub}$, are applied (e.g., $V_{sub}<<0$) the controllable inversion layer 116 may shrink to a thickness $t_3$, $t_3<t_2<t_1$. The thickness $t_3$ may be a limit where the sensitivity of the sensing layer 112 is at a maximum. It should be noted that the thicknesses of the controllable inversion layer 116 are shown as having discrete boundaries or dimensions for ease of explanation and illustration. However, in practice, the thickness of the controllable inversion layer 116 may be more gradual. In other words, the boundary between the controllable inversion layer 116 and the pure silicon in the body 104 may have a visible transition.

In one example, the sensing layer 112 may be electrically floating and can be engineered to be sensitive to a target gas, where interactions can lead to reversible changes in work-function and/or morphology. In one example, the sensing layer 112 may be ultra-thin (<5 nanometers (nm)) and composed of nickel (Ni) (0.3 nm) and palladium (Pd) (1 nm) and used as a hydrogen sensitive sensing layer, where the hydrogen dissociates over Pd very readily at room temperature into atomic hydrogen leading to the formation of $PdH_x$.

Here, CS-FETs are configured as n-type transistors with light p⁻ body doping (~8e14 centimeters (cm⁻³) boron atoms) and the electrically floating sensing layer 112 is capacitively coupled to the silicon channel via the native oxide layer 110 (estimated effective oxide thickness ~2.5 nanometers (nm)). In one example, the wafer doping concentration may correlate to a resistivity of approximately 10-30 ohm-cm. Under equilibrium and ambient conditions, the CS-FET threshold voltage ($V_t$) is determined by the doping in the body 104 and effective work-function (EWF) of the sensing layer 112, which for ultra-thin Ni—Pd is expected to be much lower (~4.2 electron volts (eV)) than bulk values (~5.11 eV) due to work-function dependence on metal thickness. If the $V_t$ is sufficiently low, an inversion layer 116 of electrons (transistor channel) is created at the Si/SiO₂ interface. The total electron density and thickness of the inversion layer 116 (which is directly dependent on $V_t$) can then be controlled by applying a reverse-bias to the silicon substrate body 104, as depicted in FIG. 1.

In device-physics, this mechanism of $V_t$-control is called the "body-effect", where an appropriate body-voltage ($V_{SUB}$) effectively controls the p-n junction formed between the p⁻ body and the n⁻ inversion-layer. From a sensors perspective, this provides a highly tunable sensitivity mechanism for CS-FETs leading to large sensor responses and sensitivities. Eq. 1 describes the relation between applied body bias and threshold voltage:

$$\Delta V_t = \frac{\sqrt{2\epsilon_s q N_a}}{C_{ox}}(-V_{SUB})^{1/2}, \quad \text{Eq. 1}$$

where $\epsilon_s$ is the dielectric permittivity of silicon, q is the electron charge, $N_a$ is the acceptor concentration (boron), $C_{ox}$ is the capacitance of the native oxide and $V_{SUB}$ is the applied body bias.

Figure 2:
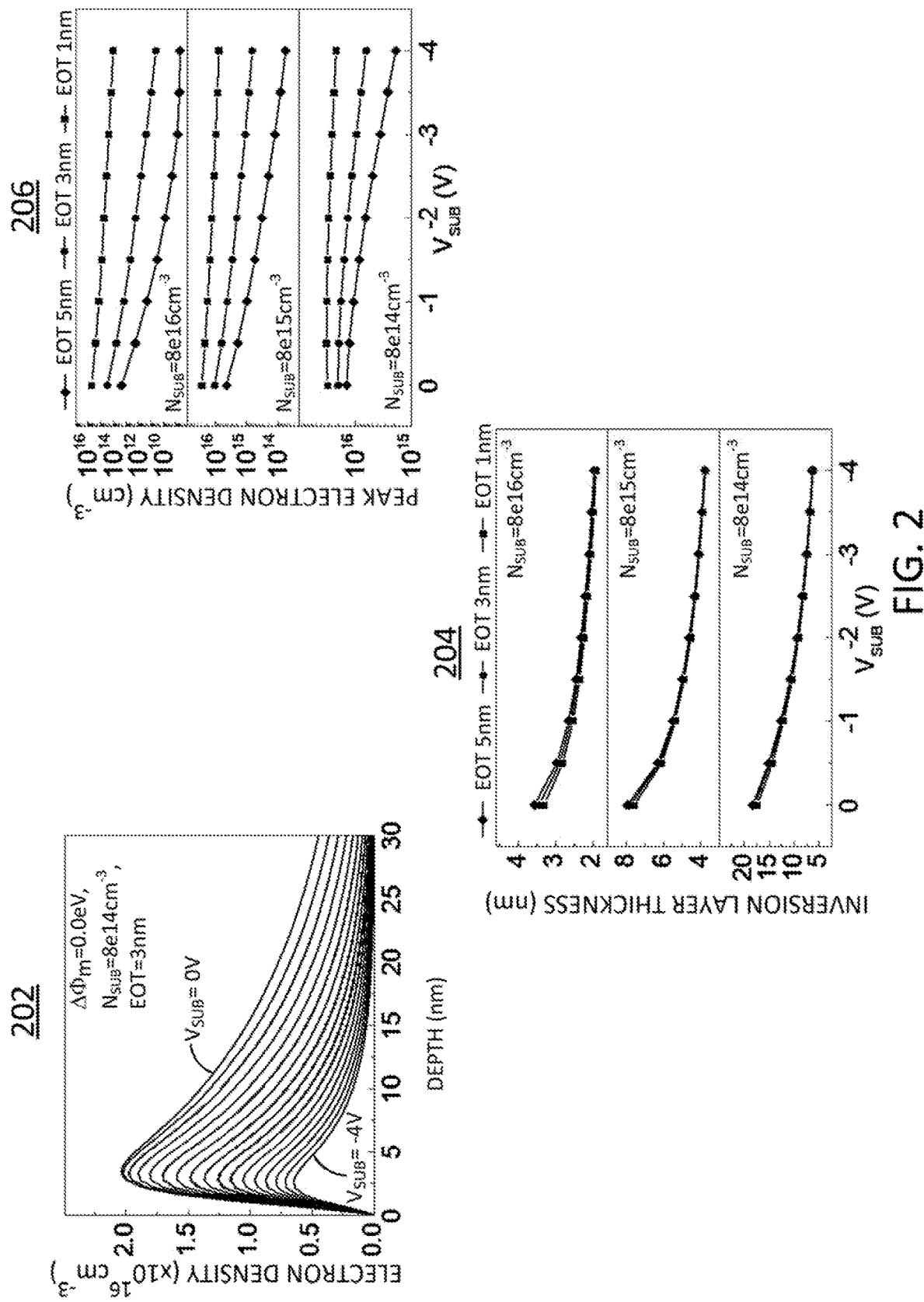
FIG. 2 illustrates different graphs of data associated with the sensing mechanism of the example bulk silicon CS-FET of the present disclosure.
Figure 3:
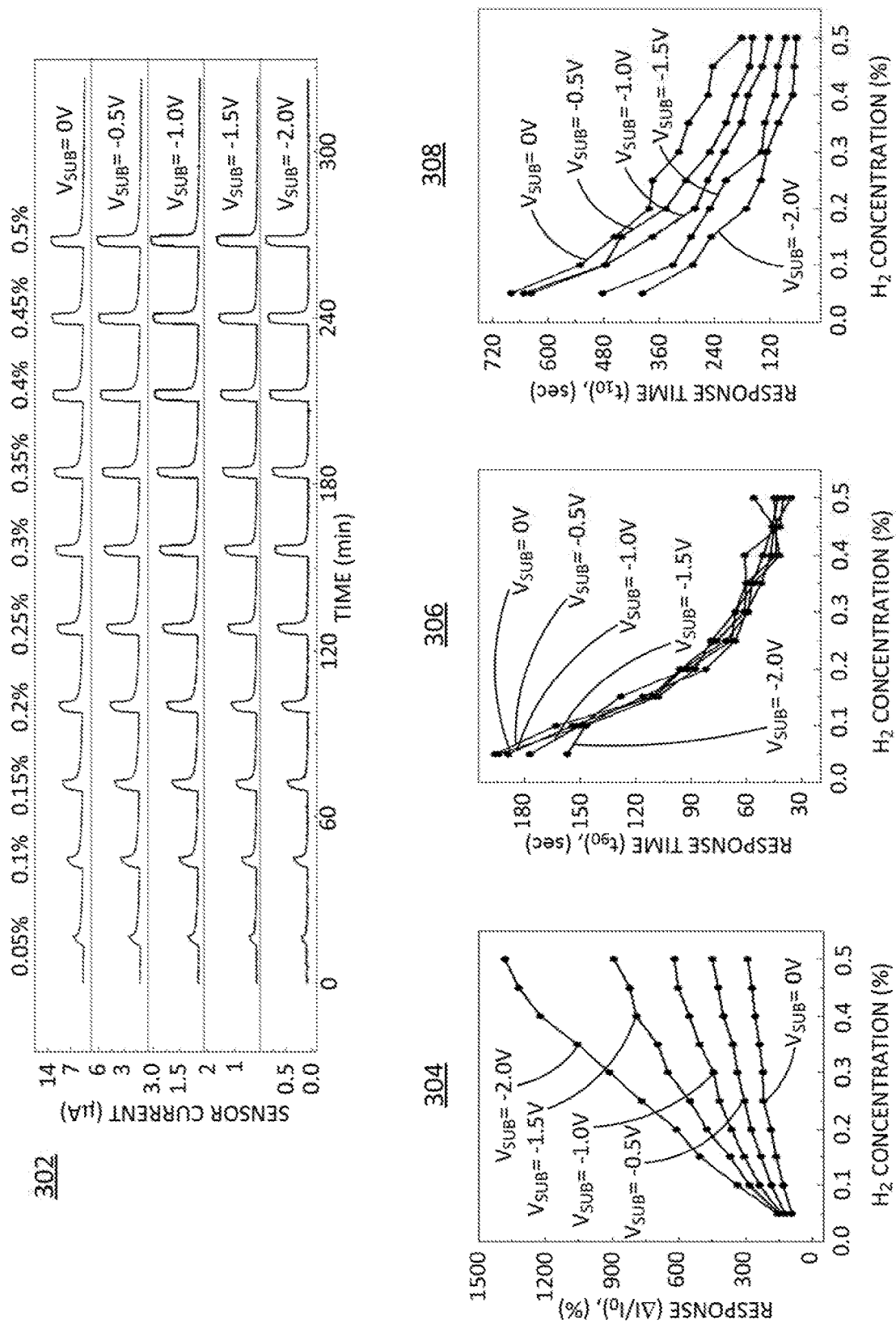
FIG. 3 illustrates different graphs of data measured from operation of the example bulk silicon CS-FET sensor of the present disclosure.

A physical understanding of the sensing mechanism in bulk silicon CS-FET gas sensors is presented in FIG. 2 using TOAD device modeling and simulations. Table 1 lists all the parameters used in simulating the n-type transistors where the effective sensing layer work-function is set at 4.2 eV to match experimental baseline sensor current values at 0V body bias (FIG. 3).

TABLE 1

CS-FET device parameters.

| | | |
|---|---|---|
| Gate length ($L_g$) | 3 μm | 3 μm |
| Device width (W) | 1 μm* | 30 μm |
| Effective oxide thickness (EOT) | 3 nm | ~3 nm |
| Source/drain doping | 1 × 10²⁰ cm⁻³, Phosphorus | ~1 × 10²⁰ cm⁻³, Phosphorus |
| Body doping ($N_{SUB}$) | 8 × 10¹⁴ cm⁻³, Boron | 6 × 10¹⁴ cm⁻³ to 1 × 10¹⁵ cm⁻³, Boron |

*Simulations are done in only two dimensions, with default channel width of 1 micron (μm).

In one example CS-FET device simulations were carried using Synopsys TOAD (Version M-2016.12). Carrier transport in devices are handled by self-consistently solving Poisson's continuity equation with the drift-diffusion model. The Philips unified model is used for calculating mobility in the devices. Quantum confinement effects associated with nanoscale devices are taken into consideration using the density-gradient based quantization model. The Slotboom and Graaff bandgap narrowing model is incorporated throughout the device. In addition to this, the doping dependent Shockley-Reed-Hall recombination model is utilized in conjunction with the Hurkx band-band tunneling model.

As it can be seen in graph 202 in FIG. 2, under 0V body bias ($V_{SUB}$) conditions, a simulated peak electron density of 2×10¹⁶ cm⁻³ is observed at an inversion layer depth of 3.25 nm with a total inversion layer thickness ($T_{inv}$) of 20.97 nm. $T_{inv}$ is extracted as the location of the charge centroid in graph 202. This electron density is extracted across the mid-point of the CS-FET silicon channel. Applying a −4V $V_{sub}$, lowers the peak electron density to 0.65×10¹⁶ cm⁻³ at an inversion layer depth of 2.732 nm and a $T_{inv}$ of ~9.34 nm. With reverse body bias, the inversion layer 116 is not only thinner, but is also pushed closer to the interface of the native oxide layer 110 and silicon by ~0.5 nm ($\Delta T_{inv}$=0.5 nm), leading to improved electrostatic control in the channel by the sensing layer 112. Furthermore, $T_{inv}$ and peak electron density in the inversion layer 116 can be tuned by the EOT and doping of the body 104 as depicted in graphs 204 and 206, where both $T_{inv}$ and peak electron density is reduced with decreasing EOT and increasing doping in the body 104.

Figure 7:
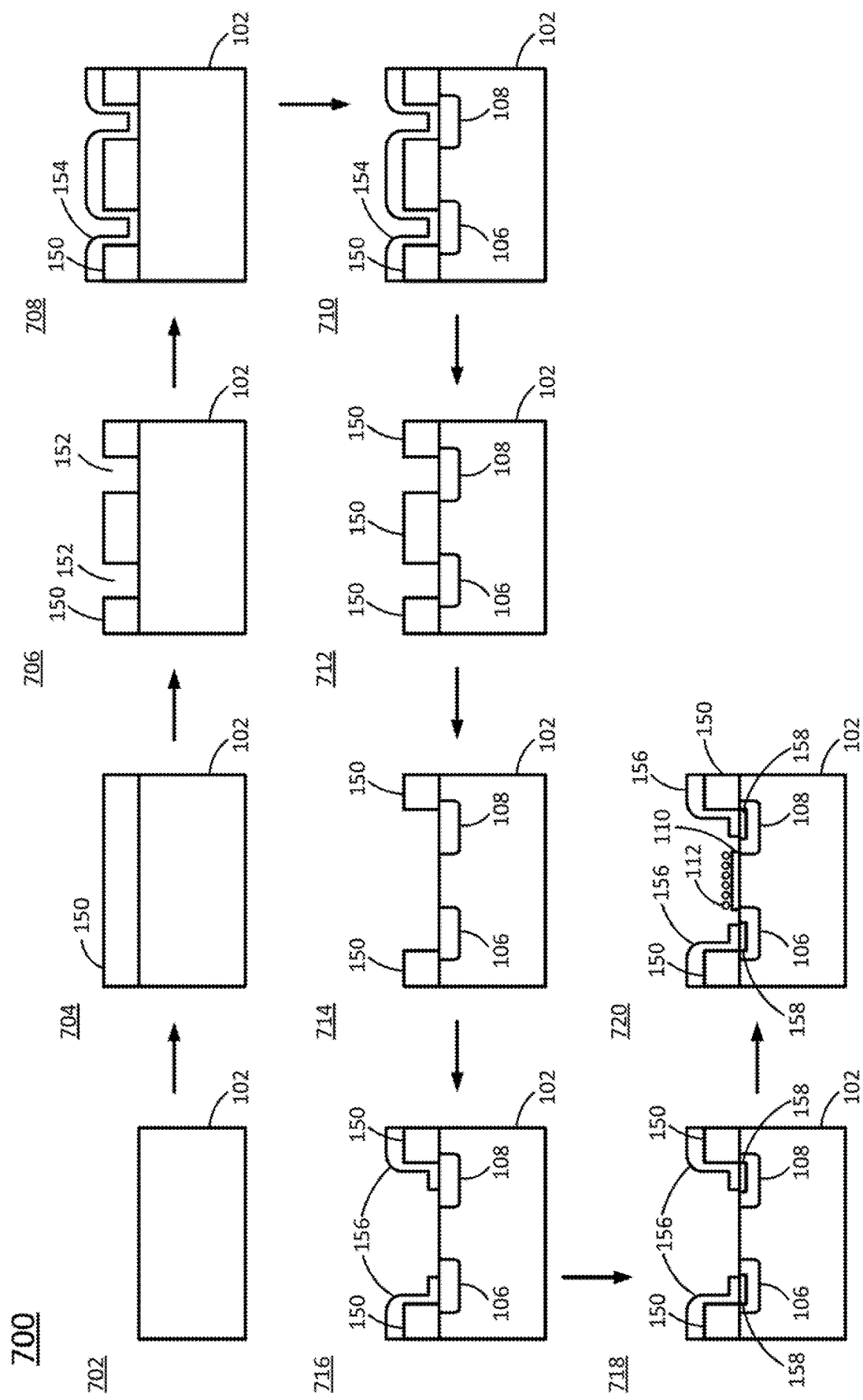
FIG. 7 illustrates an example process flow of a method for fabricating the example bulk silicon CS-FET of the present disclosure.

Bulk silicon CS-FETs are fabricated using a fully CMOS-compatible, gate-last processing scheme (as shown in FIG. 7, and discussed in further details below), where the Ni—Pd sensing layer is deposited in the last process step. A graph 302 in FIG. 3 shows the experimentally measured room-temperature sensor response of a Ni.Pd CS-FET to different concentrations of hydrogen ranging from 0.05% to 0.5% in steps of 0.05%, at different body biases.

With increasing reverse body bias, sensor linearity is drastically improved as indicated in graph 304, where the sensitivity increases from 0.04%/ppm to 0.27%/ppm upon changing body biases from 0 volts (V) to −2V. Here, sensitivity is defined as the approximate slope of % sensor response $(I_{peak}-I_{baseline})/I_{baseline}$) per ppm of hydrogen gas.

The graph 306 shows the sensor response time ($t_{90}$) vs. hydrogen concentration, with minimum and maximum $t_{90}$~36 s (for 0.5% $H_2$) and 196 s (for 0.05% $H_2$) respectively. Varying the body bias appears to have no significant effect on sensor response time. This is expected, as response times are highly dependent on the rate at which hydrogen adsorbs and dissociates over the Ni—Pd sensing layer.

The graph 308 depicts the room temperature recovery times ($t_{10}$) from different hydrogen concentrations, with minimum and maximum $t_{10}$ of ~62 s (for 0.5% $H_2$) and 679 s (for 0.05% $H_2$) respectively. Contrary to the data in the graph 306, varying the body bias has a dramatic effect on sensor recovery times, with larger reverse biases enabling faster recovery times. In all of the above measurements, the total power consumption of the hydrogen sensors is below 50 microwatts (µw), re-affirming bulk silicon CS-FETs as a highly competitive low power gas sensing platform.

Figure 4:
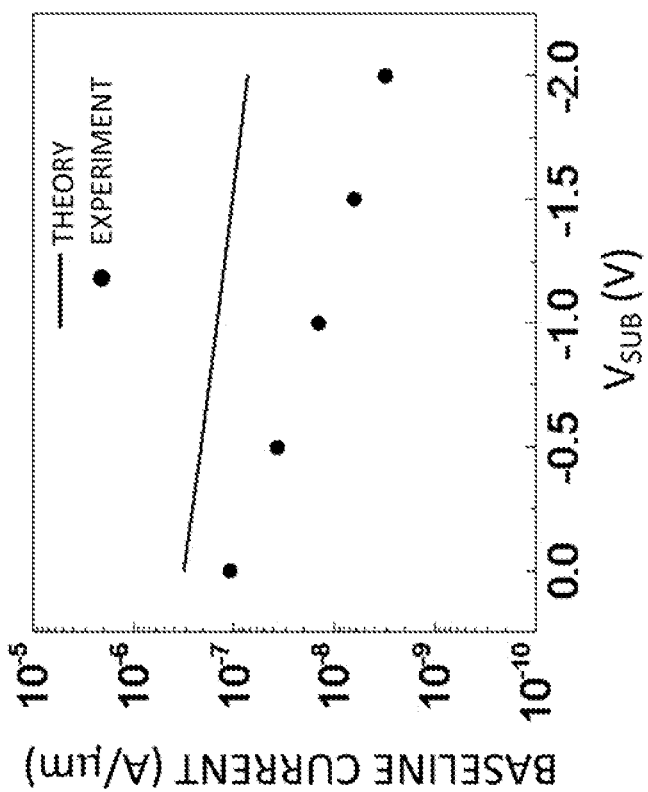
FIG. 4 illustrates different graphs of data for theory versus experiments of the example bulk silicon CS-FET of the present disclosure.
Figure 4:
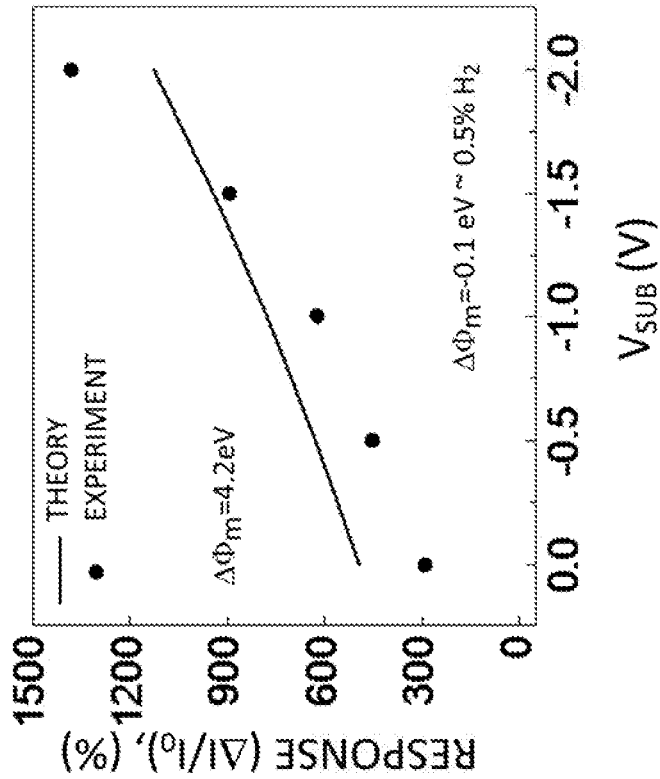

The graph 402 in FIG. 4 compares the experimental data in the previous section with theory, where simulated sensor responses are obtained at different body biases for a constant −0.1 eV work-function change in the sensing layer 112 (analogous to a simulated gas exposure of 0.5% $H_2$). As mentioned previously, the sensing layer work-function in the simulations is set at 4.2 eV, based on the closest match between the simulated and experimental baseline drain currents, at 0V body bias ($V_{SUB}$=0V) and 3V drain bias ($V_{DS}$=3V). While the simulated and experimental baseline currents are very close in value at $V_{SUB}$=0V (as shown in graph 404), varying the body bias indicates a discrepancy between the two, where experimental baseline currents drop more sharply with large reverse bias compared to theory. It may be hypothesized that this discrepancy may be because of environmental/ambient effects on the experimental sensor characteristics which are difficult to capture in theoretical simulations. Nonetheless, the trend of decreasing sensor currents and increasing sensor responses with higher reverse body bias is consistent in both theory and experiment.

Figure 5:
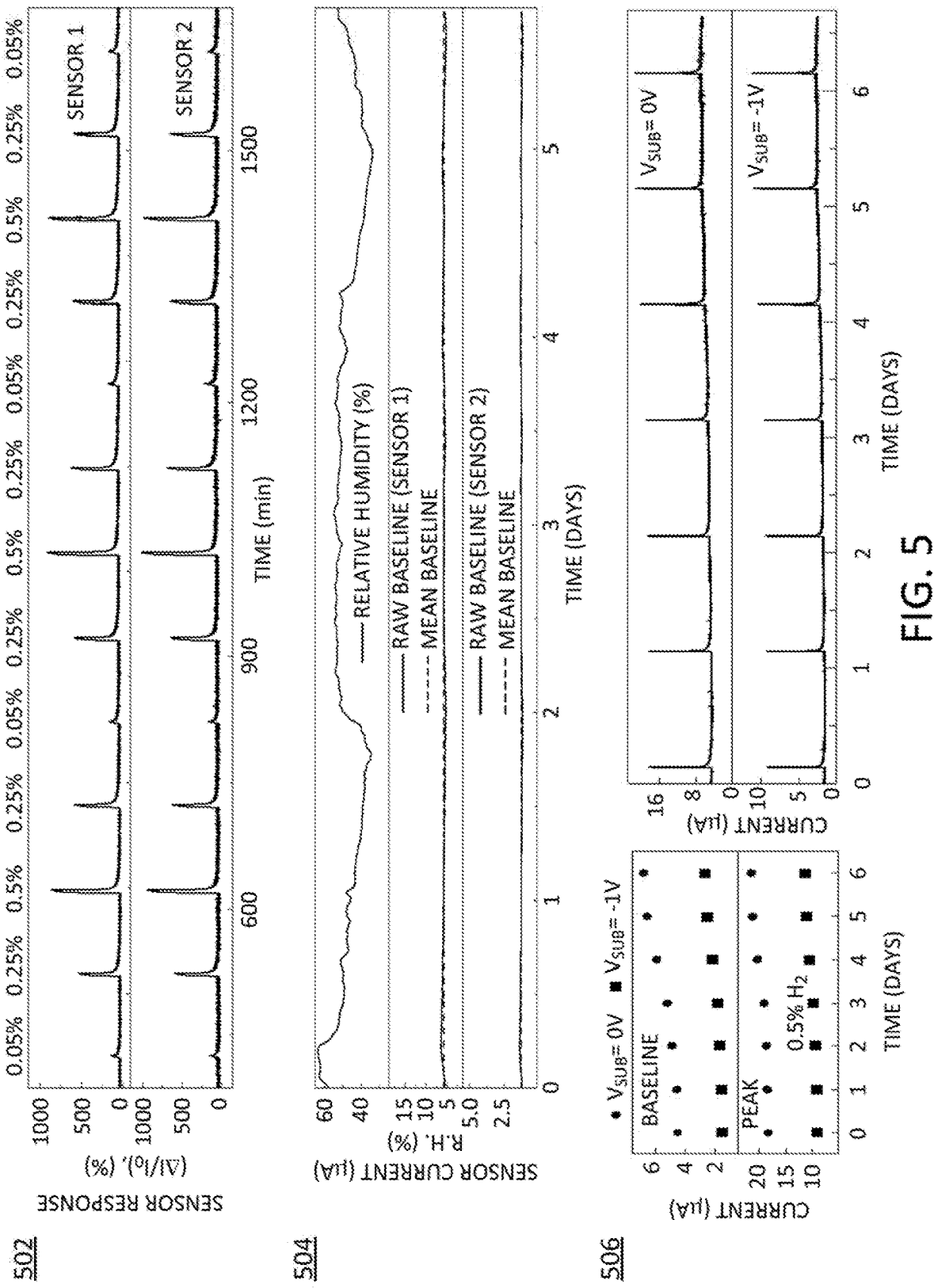
FIG. 5 illustrates different graphs of data related to gauge sensor hysteresis and long-term stability of the example bulk silicon CS-FET of the present disclosure.

Several experiments were conducted to gauge sensor hysteresis and long-term stability. Exposing the sensor to cycles of low, medium and high concentrations of hydrogen indicates minimal hysteresis in sensor performance as indicated by a graph 502 in FIG. 5, where two different Ni—Pd CS-FET sensors are exposed to three cycles of 0.05%, 0.25% and 0.5%.

The graph 504 captures the baseline drift of two sensors ($V_{DS}$=3V, $V_{SUB}$=0V) over a period of 5.7 days, where the sensors were measured in still air without any gas flow and uncontrolled room humidity. The maximum variation from mean baseline current in both sensors is approximately 10%, indicating very stable sensor baselines.

The graph 506 shows the variation in peak sensor response current to a fixed hydrogen concentration for nearly a week, where a Ni—Pd sensor is exposed to 0.5% $H_2$ (for 10 minutes) once per day. This measurement is carried out room temperature and the relative humidity is uncontrolled and fluctuates between 20%-40%.

Figure 6:
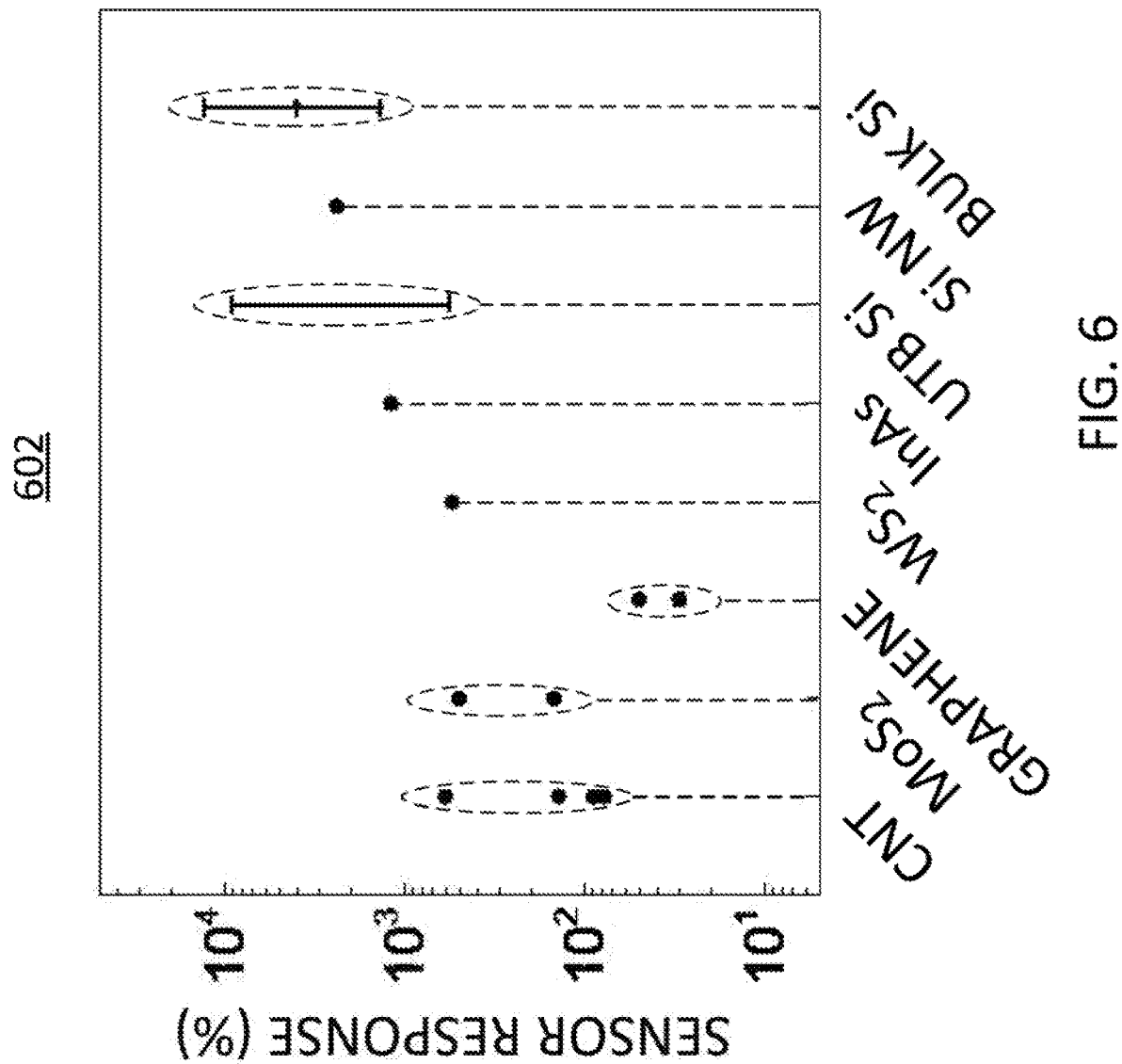
FIG. 6 illustrates a comparison of benchmark performance of the bulk silicon CS-FET of the present disclosure compared to other emerging materials.

Finally, the benchmarked performance of bulk silicon CS-FETs were compared against emerging materials for low power miniaturized gas sensing. As indicated by a graph 602 in FIG. 6, bulk silicon has comparatively better performance in terms of normalized sensor response (%). This benchmark plot cites research works that have used both functionalized and non-functionalized emerging materials like CNTs, $MoS_2$, graphene, etcetera, for hydrogen gas sensing at the same concentration (0.5%). It should be noted that for FET based sensors, high sensitivity can be achieved by proper $V_t$-control, regardless of the semi-conducting channel material and as the long the material does not contribute to the overall chemical sensor response. This is why conventional bulk silicon is able to outperform low dimensional materials in FIG. 6.

FIG. 7 illustrates an example process flow for a method 700 for fabricating the example bulk silicon CS-FET gas sensor of the present disclosure. For example, at block 702, the method 700 may start with a silicon substrate 102. The silicon substrate may have an average resistivity associated with a wafer doping concentration of approximately 8e14 centimeters ($cm^{-3}$) boron atoms. In one example, the silicon substrate 102 may have a resistivity of approximately 10-30 ohm-cm.

At block 704, the method 700 may grow a silicon oxide layer 150 on the surface of the silicon substrate 102. At block 706, the method 700 may pattern and etch the silicon oxide layer 150 using known lithography processes and etching processes (e.g., wet etch, dry etch, and the like). The patterning and etching may create openings 152 in the silicon oxide layer 150.

At block 708, the method 700 may deposit a layer of phosphorous silicide glass (PSG) 154 on the patterned silicon oxide 150 and the silicon 102 that is exposed by the openings 152. The PSG 154 may be deposited using a low pressure chemical vapor deposition (LPCVD) process.

At block 710, the method 700 may dope the silicon for n-type wells or p-type wells. FIG. 7 illustrates an example, where n-type wells 106 and 108 are formed using a drive-in anneal process to form n++ source/drain (S/D). At block 712, the method 700 may strip the PSG layer 154 using selective etching.

At block 714, the method 700 may pattern and etch the silicon substrate 102 (e.g., using known lithography and etching processes) to open an undoped channel region wherein the sensor layer 112 may eventually be deposited. At block 716, the method 700 may pattern and etch recessed regions for nickel e-beam deposition and lift-off for S/D metallization. For example a layer of nickel 156 may be applied to the silicon oxide layers 150 for the patterning and etching.

At block 718, the method 700 may perform a forming gas anneal (FGA) for nickel silicide (NiSi) to complete the S/D metallization. Thin metal-silicide layers 158 may be formed at the interface between the nickel 156 and the wells 106 and 108. The metal silicide layers 158 may be nickel silicide.

At block 720, the method 700 may form a silicon dioxide layer 110 on the undoped channel region and deposit the sensing layer 112 on the silicon dioxide layer 110. The method 700 may also perform an anneal process in nitrogen gas or FGA. In one example, the nickel layers 156 and the silicon oxide layers 150 may also be etched away to form the final gas sensor 100 as shown in FIG. 1.

Thus, the present disclosure demonstrates a gas sensor fabricated as a chemical sensitive field effect transistor on bulk silicon, with an electrically floating ultra-thin $Ni_{0.3\ nm}Pd_{1\ nm}$ sensing layer for $H_2$ gas sensing. Through device modeling and simulations, the present disclosure demonstrates that by applying a reverse body bias, the sensitivity of the CS-FET can be tuned electrically. This has been corroborated by measuring the $H_2$ sensor response of fabricated Ni—Pd CS-FETs at different body biases, resulting in improved sensor linearity and recovery times. Through concentration cycling, the present disclosure has shown that this platform has minimal sensor hysteresis and long term ambient measurements indicate minimal drift with approximately 10% variation from mean baseline current values. The results presented in the present disclosure demonstrate a gas sensor that is fabricated from bulk silicon CS-FETs from both a performance and a manufacturability perspective, opening up new opportunities in highly miniaturized single-chip multiplexed gas sensors for a wide variety of applications in industrial safety, environmental air quality monitoring, wireless sensor networks and consumer electronics.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A gas sensor, comprising:
   a bulk silicon layer, comprising a controllable inversion layer;
   an oxide layer on top of the bulk silicon layer, wherein the controllable inversion layer is located at an interface of the bulk silicon layer and the oxide layer, wherein the oxide layer has a thickness of approximately 2-3 nanometers; and
   a sensing layer on the oxide layer, wherein the sensing layer has a thickness of less than 5 nanometers, wherein a sensitivity of the sensing layer is a function of a thickness of the controllable inversion layer comprising a transistor channel of electrons at the interface of the bulk silicon layer and the oxide layer, wherein a negative voltage that is applied reduces the thickness of the controllable inversion layer and increases the sensitivity of the sensing layer by changing a density of the electrons.

2. The gas sensor of claim 1, wherein a sensitivity of the gas sensor is tunable by controlling an amount of voltage applied to the bulk silicon layer to change the thickness of the controllable inversion layer below the sensing layer.

3. The gas sensor of claim 1, wherein the bulk silicon layer comprises n-doped wells and a body of the bulk silicon layer is p-doped.

4. The gas sensor of claim 3, wherein the negative voltage is applied to the body of the bulk silicon layer.

5. The gas sensor of claim 4, wherein the controllable inversion layer increases in sensitivity as the thickness of the controllable inversion layer decreases as an amount of the negative voltage increases.

6. The gas sensor of claim 1, wherein the sensing layer is electrically floating.

7. The gas sensor of claim 1, wherein the sensing layer comprises nickel and palladium to detect hydrogen gas.

8. A gas sensor, comprising:
   an n-doped bulk silicon layer having a p-doped body, wherein the n-doped bulk silicon layer comprises a controllable inversion layer;
   an oxide layer on top of the controllable inversion layer of the n-doped bulk silicon layer, wherein the oxide layer has a thickness of approximately 2-3 nanometers; and
   a sensing layer on the oxide layer, wherein the sensing layer has a thickness of less than 5 nanometers, wherein a sensitivity of the sensing layer is a function of a thickness of the controllable inversion layer comprising a transistor channel of electrons at an interface of the p-doped body of the n-doped bulk silicon layer and the oxide layer, wherein a negative voltage that is applied reduces the thickness of the controllable inversion layer and increases the sensitivity of the sensing layer by changing a density of the electrons.

9. The gas sensor of claim 8, wherein the thickness of the controllable inversion layer comprises an inverse relationship to an amount of the negative voltage applied to the p-doped body.

10. A method for adjusting a sensitivity of a sensing layer of a gas sensor comprising a bulk silicon layer comprising a controllable inversion layer, an oxide layer on top of the bulk silicon layer, wherein the controllable inversion layer is located at an interface of the bulk silicon layer and the oxide layer, and a sensing layer on the oxide layer, comprising:
    applying a voltage to a well of the bulk silicon layer to cause a thickness of the controllable inversion layer to change from an initial thickness when zero volts are applied to the well, wherein a change in the thickness of the controllable inversion layer changes a sensitivity of the sensing layer.

11. The method of claim 10, wherein the well is n-doped, the voltage is a negative voltage, and the thickness of the controllable inversion layer is less than the initial thickness to increase the sensitivity of the sensing layer.

* * * * *